(12) United States Patent
Mazzara

(10) Patent No.: US 7,717,876 B2
(45) Date of Patent: May 18, 2010

(54) RETRACTABLE NEEDLE SAFETY SYRINGE

(76) Inventor: Isidoro Mazzara, Via XXV Aprile, 13, Campofranco (Caltanissetta) (IT) I-93010

(*) Notice: Subject to any disclaimer, the term of this patent is extended or adjusted under 35 U.S.C. 154(b) by 50 days.

(21) Appl. No.: 11/718,771

(22) PCT Filed: Nov. 24, 2005

(86) PCT No.: PCT/IT2005/000688
§ 371 (c)(1),
(2), (4) Date: May 30, 2007

(87) PCT Pub. No.: WO2006/057025
PCT Pub. Date: Jun. 1, 2006

(65) Prior Publication Data
US 2008/0033355 A1    Feb. 7, 2008

(30) Foreign Application Priority Data
Nov. 24, 2004    (IT) .......................... BS2004A0143

(51) Int. Cl.
*A61M 5/00* (2006.01)
(52) U.S. Cl. ........................................ 604/110
(58) Field of Classification Search ................. 604/110, 604/192–198
See application file for complete search history.

(56) References Cited

U.S. PATENT DOCUMENTS

| 3,186,408 A | | 6/1965 | Jacob |
| 5,190,526 A | * | 3/1993 | Murray et al. ............... 604/110 |
| 6,193,695 B1 | | 2/2001 | Rippstein, Jr. |
| 7,267,664 B2 | * | 9/2007 | Rizzo .......................... 604/110 |

FOREIGN PATENT DOCUMENTS

| DE | 4314395 | 12/1994 |
| EP | 0505330 | 9/1992 |
| EP | 1461100 | 9/2004 |
| FR | 2727021 | 5/1996 |
| IT | 1248456 | 1/1995 |

* cited by examiner

*Primary Examiner*—Matthew F Desanto
(74) *Attorney, Agent, or Firm*—Shoemaker and Mattare

(57) ABSTRACT

The invention relates to a perfected retractable needle safety syringe comprising a hollow cylinder, a needle holder, a needle and a piston with an operating stem, said stem exhibiting an axial hole wherein there are seated a retraction preloaded spring and an extractor element. The extractor element exhibits a recess or seat intended for interacting with the needle holder, and at the side opposite the needle holder, a projection or annular rib.

13 Claims, 5 Drawing Sheets

RETRACTABLE NEEDLE SAFETY SYRINGE

FIELD OF THE INVENTION

This invention relates to retractable needle safety syringes which prevent further use of a syringe after a first use.

BACKGROUND ART

Retractable needle syringes are already known from former patents by the owner of the present application.

One of them is disclosed in Italian patent no. 1,248,456 and another one in Italian patent no. 1,288,237.

The solutions described in these patents, however, have construction and structural problems that make their construction particularly complex and expensive and, above all, do not always ensure a safe and regular operation due to such complexity.

SUMMARY OF THE INVENTION

The object of the present invention is to provide a retractable needle safety syringe having a simpler and more rational construction by the use of functional devices which, although simple from the construction point of view, increase the safety of use.

Such object is achieved with a retractable needle safety syringe as described below.

BRIEF DESCRIPTION OF THE DRAWINGS

Further details of the invention are provided in the following description of a preferred embodiment, made by way of a non-limiting example with reference to the annexed drawing, wherein.

DETAILED DESCRIPTION OF A PREFERRED EMBODIMENT

Figure 1:
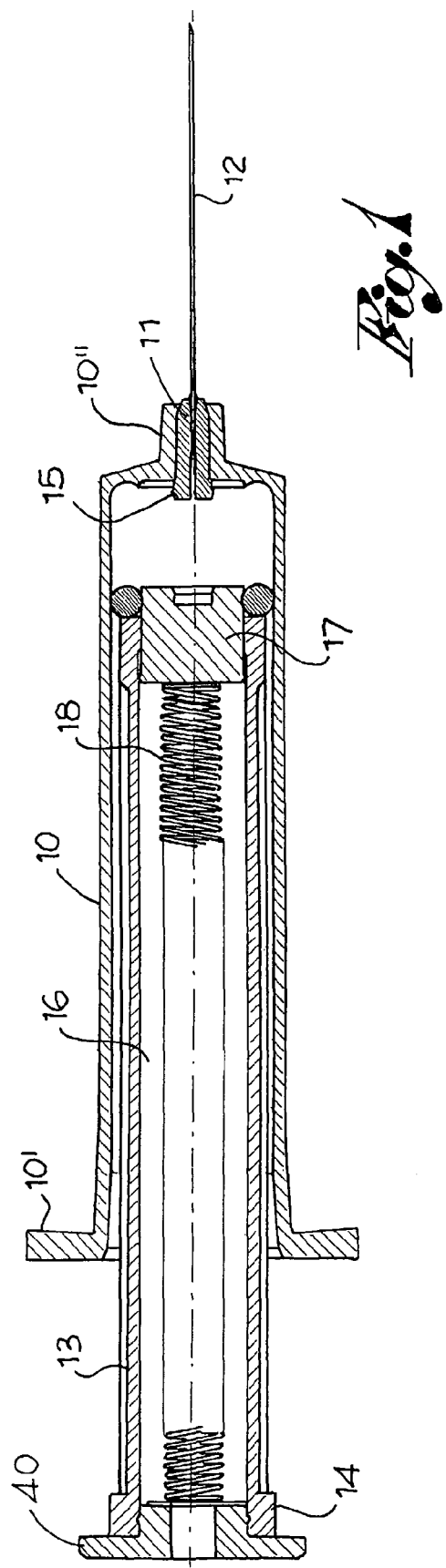
FIG. 1 shows an axial section view of the syringe according to the invention in the condition immediately prior to its use.
Figure 2:
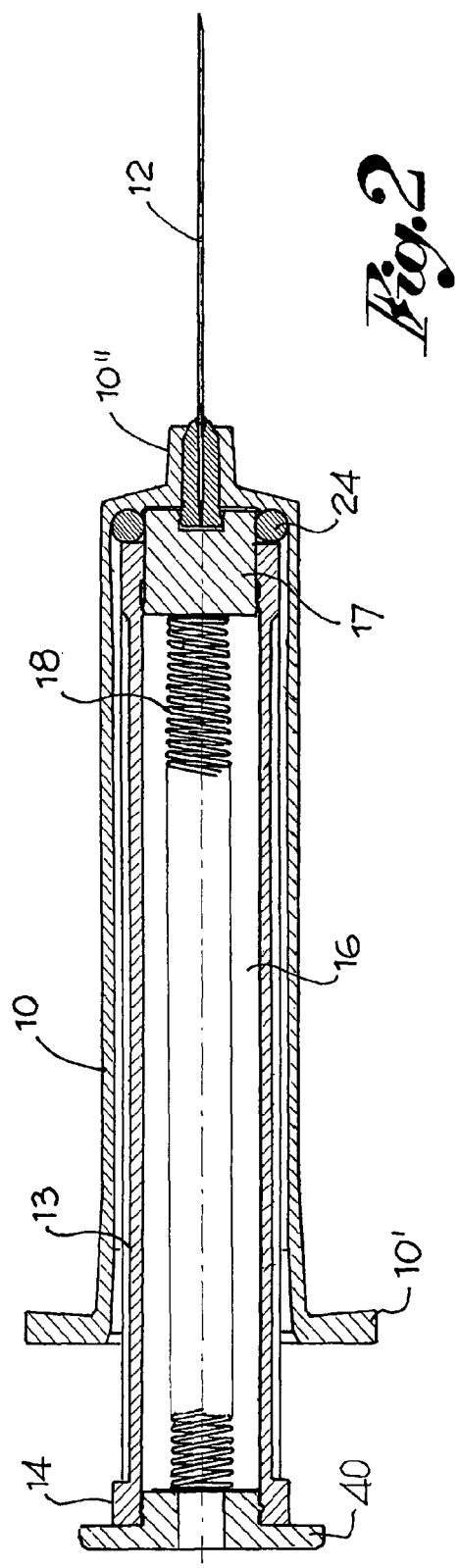
FIG. 2 shows the syringe after use.

FIG. 1 shows a syringe comprising a hollow cylinder 10, a needle holder 11, a needle 12 and a piston 13 with an operating stem 14.

The hollow cylinder 10 has at the back, that is, at the end opposite needle 12, a gripping flange 10' and at the front it ends with a collar 10" inside which there is suitably seated the needle holder 11 integral with needle 12. The needle holder 11 has an end portion 15 facing the interior of the hollow cylinder 10 and is intended for allowing the retraction thereof, as explained hereinafter. It should be noted that the hollow cylinder 10 exhibits an increase of the internal diameter in the end portion thereof facing the needle holder 11. This allows both proper suction and the full compression of the substance to be injected. Moreover, as described hereinafter, this increase of internal diameter aids the proper coupling of the needle holder 11.

Advantageously, needle 12 is secured to the needle holder 11 by gluing. For example, the latter exhibits a flared tip 11' which aids the introduction of needle 12 from the outside and which is then filled with a suitable amount of glue 44.

The operating stem 14 further has an axial hole 16 in whose end portion facing the needle holder 11 there is seated an extractor element 17 connected to a retraction pre-loaded spring 18. Said spring 18 thus tends to pull the extractor element inside the axial hole 16 of the operating stem 14.

According to a preferred embodiment, spring 18 is a cylindrical helical spring and at the end opposite the extractor element, it is connected to a cap 40 that closes piston 13 at the back.

The extractor is held in position inside the end portion of stem 14 thanks to an internal annular tooth 23' formed inside the stem 14. Tooth 23' forms an abutment for an annular projection 33 formed on the extractor element 17.

Advantageously, tooth 23' joints with the inner wall of stem 14 by an inclined plane 23" facing the annular projection 33.

Preferably, moreover, tooth 23' defines, together with a shoulder 21' obtained in stem 14, an internal annular recess 32 wherein the annular projection 33 of the extractor element 17 is free to slide axially.

In other words, stem 14 pulls the extractor element 17 in the axial movement thereof inside the hollow cylinder 10 in both directions.

The extractor element 17 has, in the portion thereof facing the needle holder 11, a recess or seat 19 intended for interacting with the end portion 15 of the needle holder 11, connecting with it after the syringe has been used.

More specifically, the recess 19 has an undercut 19' and a seating aperture 19".

Piston 13, moreover, is associated with a sealing element 24 cooperating with the inner wall of the hollow cylinder 10.

According to a particularly advantageous embodiment, the sealing element is a simple O-ring. Preferably, said O-ring 24 is mounted about a portion of the extractor element 17 protruding from the axial hole 16 into stem 14. Advantageously, an annular groove 24' for seating O-ring 24 is provided in said extractor element 17. It should be noted that the compression of O-ring 24 between the inner wall of the hollow cylinder 10 and the extractor element 17 determines a calibrated interference suitable for allowing O-ring 24 to always remain constrained to piston 13 during the axial movements thereof in both directions.

Needle holder 11 is normally axially constrained to collar 10" thanks to the interaction between a tooth 20 that extends from the inner surface of said collar 10" and a corresponding recess 21 provided in needle holder 11.

Said needle holder 11 further has at least one slot 22 such as to impart radial elasticity to the end portion 15 of needle holder 11. The slot 22 is necessary to enable the substance to be injected to easily flow through the needle without generating considerable hydrostatic pressures such as to decrease the elasticity of needle holder 11.

In turn, the end portion 15 exhibits a substantially truncated cone shape with a step or undercut 23, said end portion 15 and said step 23 being intended for seating and engaging with recess 19 provided on extractor 17.

According to a preferred embodiment, the front bottom wall of the hollow cylinder 10 has a flat abutment portion 41 for the extractor element 17 and a substantially semi-cylindrical annular seat 42 suitable for receiving O-ring 24 when piston 13 reaches the advanced stroke end portion.

The operation of the syringe is clearly shown in FIGS. 3-6.

Figure 3:
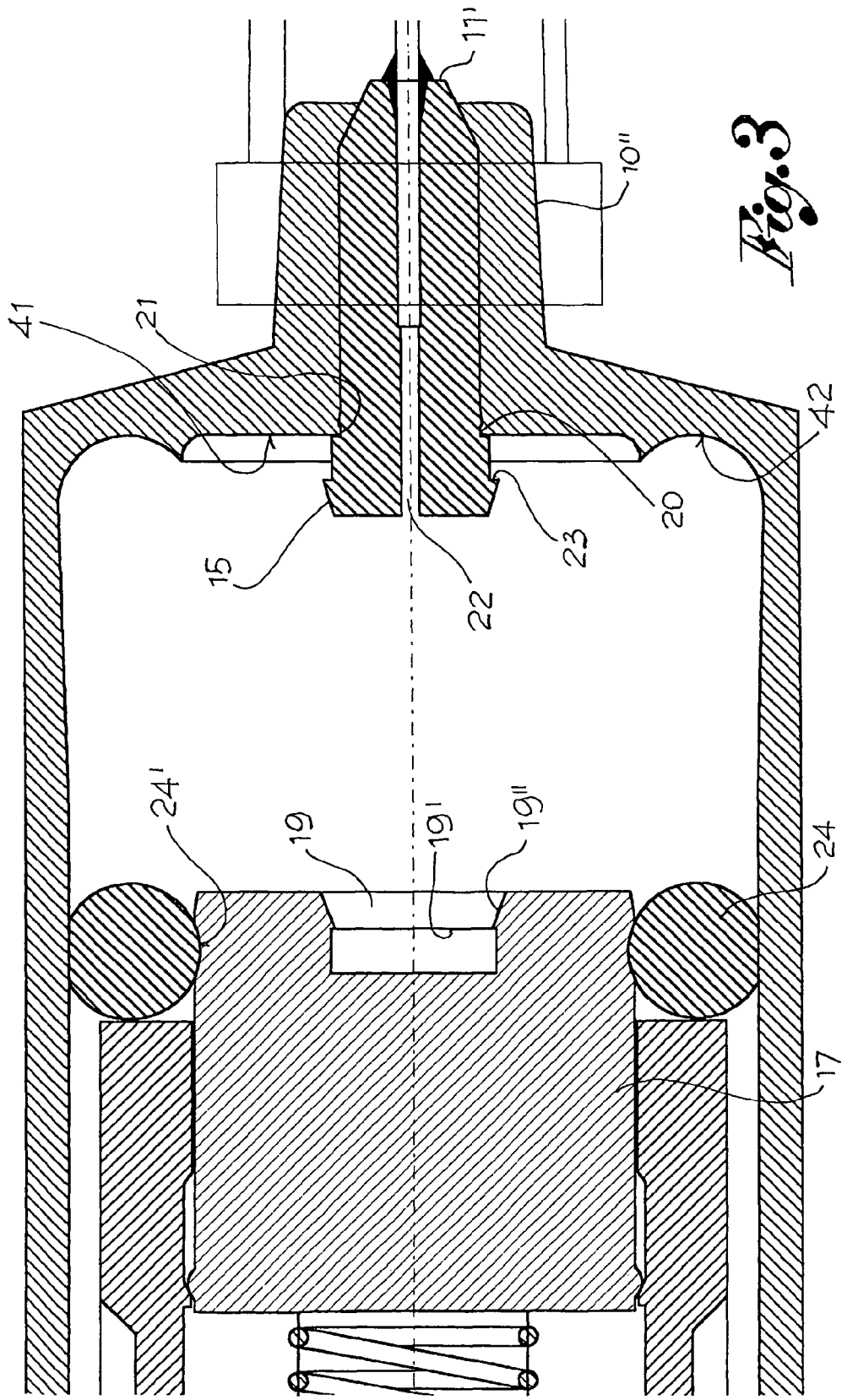
FIG. 3 shows a section view of an enlarged detail of the syringe head in the condition shown in FIG. 1.

FIG. 3 shows the condition immediately prior to the use of the syringe, wherein extractor 17 has not reached the end of stroke.

Figure 4:
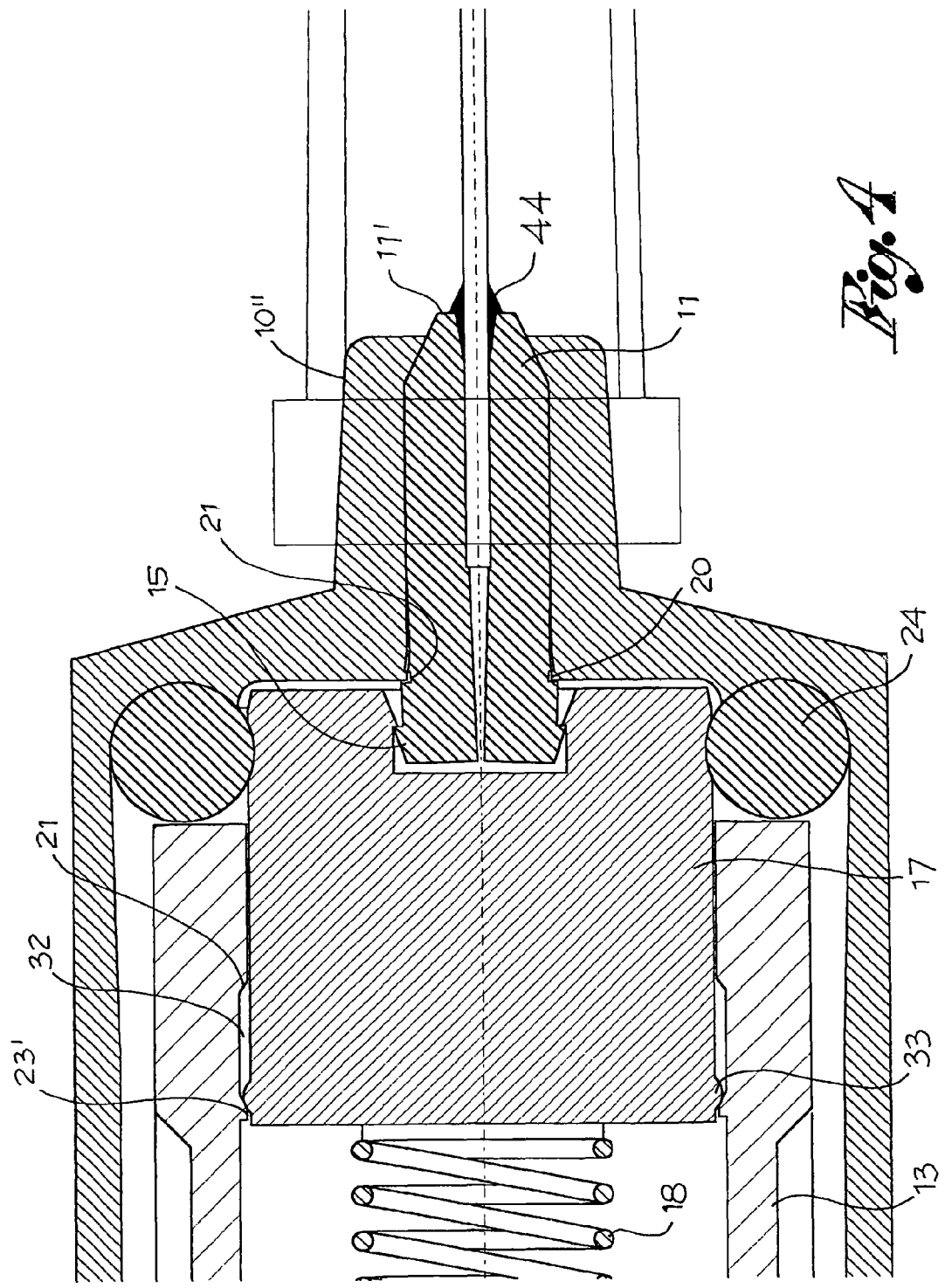
FIG. 4 shows a section view of an enlarged detail of the syringe head in the condition shown in FIG. 2.

The condition shown in FIG. 4 describes the moment when stem 14 has reached the useful stroke end. Extractor 17 is pushed forward so that the end portion 15 of needle holder 11 seats into recess 19 after the deformation thereof, elastically obtained due to the presence of slots 22 and so that it remains constrained thereto thanks to the interaction between step 23 and undercut 19'.

Due to the compressibility of the sealing element 24, it is then possible to further push stem 14 forward relative to the extractor element 17 so that tooth 23' of stem 14 goes beyond the annular projection 33 of the extractor element 17. The latter is then free to retract into the axial hole 16 pulled by the return spring 18. The force of said spring 18 is selected so as to overcome the coupling between tooth 20 of needle holder 11 and recess 21 of collar 10", so that the extractor element 17 pulls the needle holder 11 inside the syringe.

Figure 5:
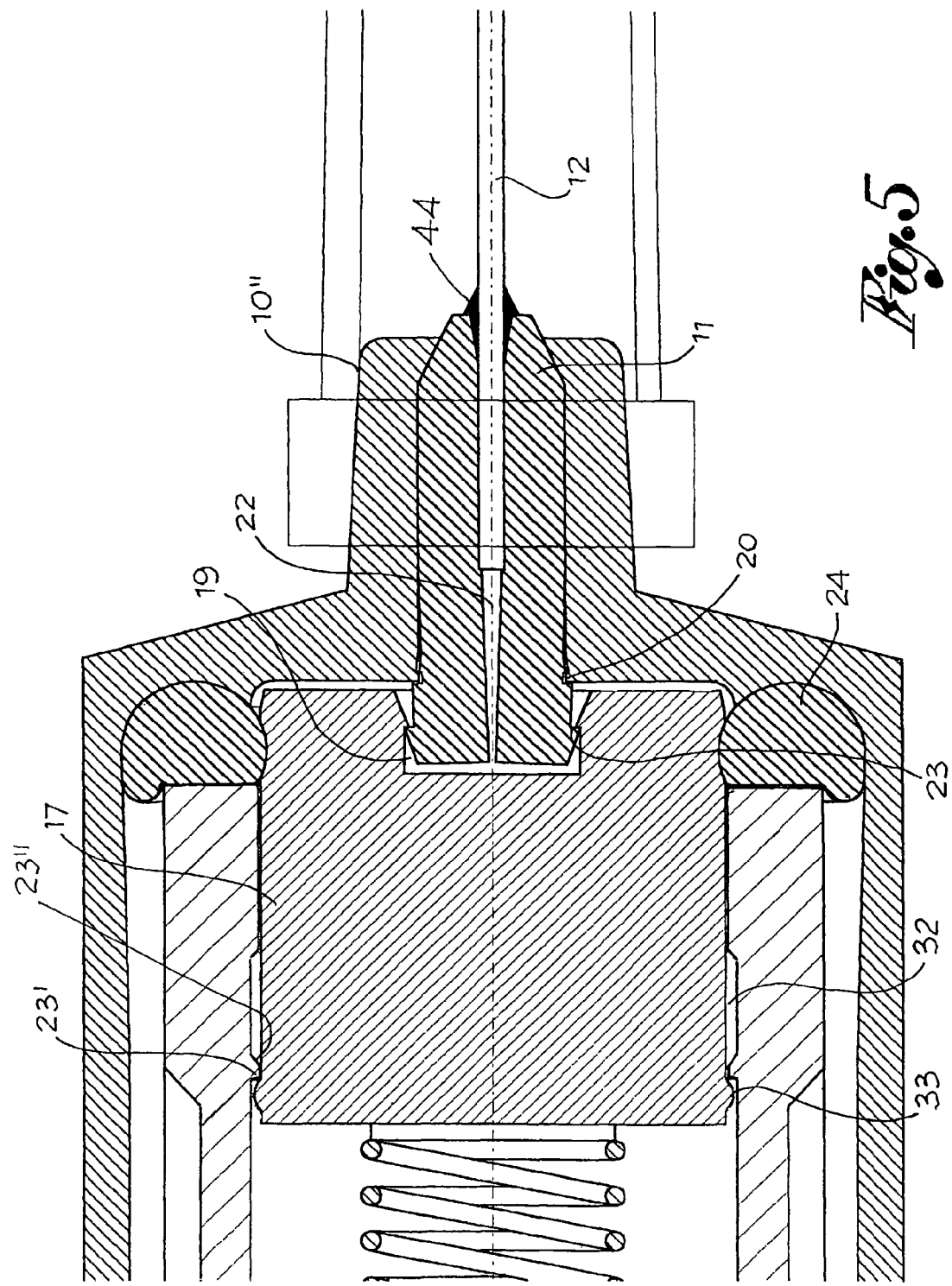
FIG. 5 shows a section view of an enlarged detail of the syringe head in the condition that allows the needle retraction.
Figure 6:
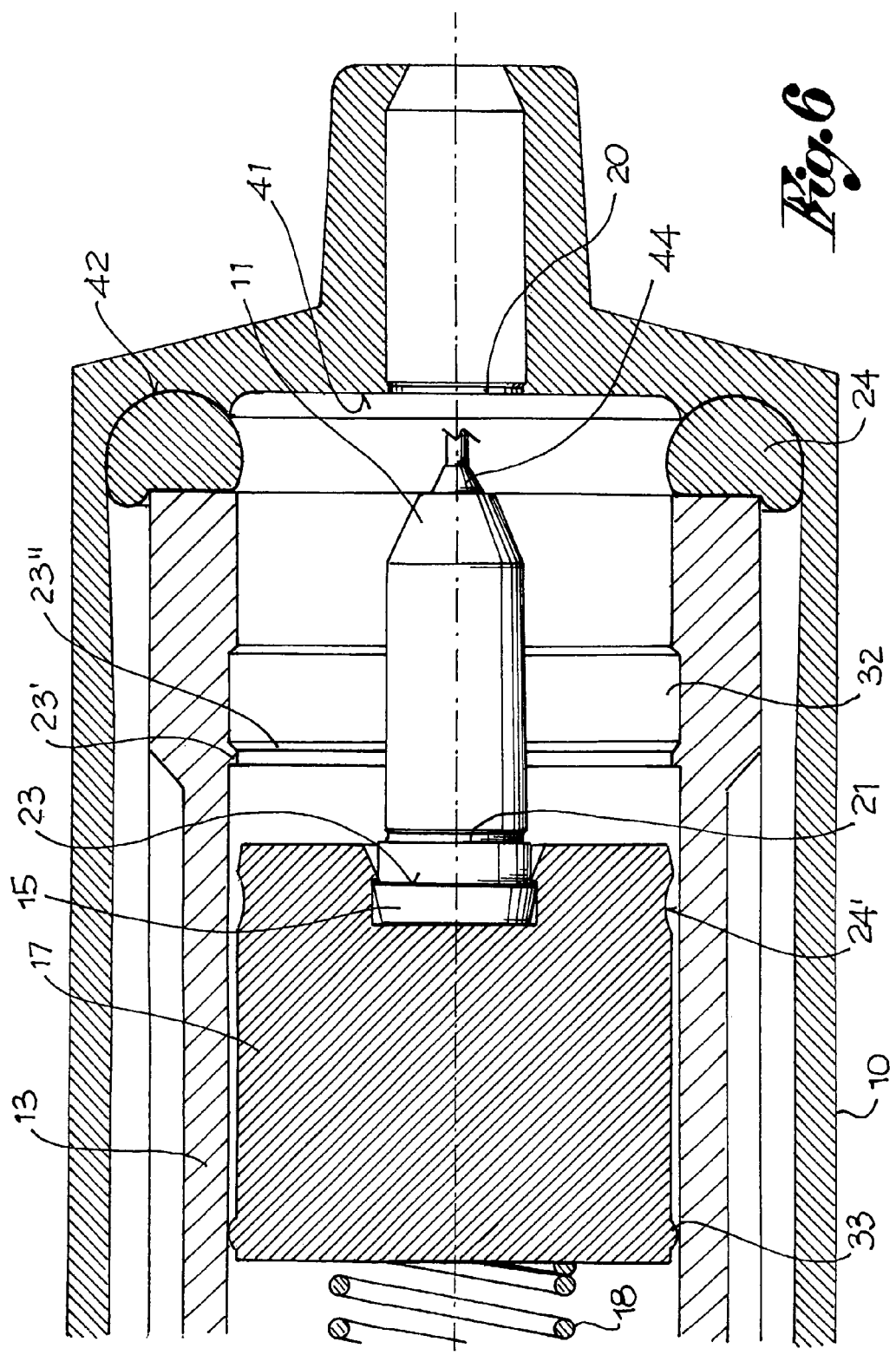
FIG. 6 shows a section view of an enlarged detail of the syringe head in the needle retraction step.

It should be noted that the increase of the inner diameter of the hollow cylinder 10 in the end portion thereof allows the sealing element 24 to radially expand when pressed by stem 14, thus allowing the further advance of the latter, as shown in FIG. 5.

On the other hand, the compression of the sealing element 24 by the operating stem 14 becomes necessary to contrast the increase of pressure of the fluid to be injected that occurs as piston 13 approaches the stroke end position.

In other words, the configuration and combination of extractor element, operating stem, sealing element and inner surface of the hollow cylinder, when the piston reaches the front stroke end position, make the residual fluid into the syringe to be considerably below the value imposed by the standards on the field.

The retractable needle safety syringe described above exhibits a particularly simple and therefore reliable structure. The needle retractable characteristic, in fact, uses the elasticity of the sealing element 24 and a suitable calibration of the force of the return spring 18 relative to the interferences between stem 14 and extractor element 17 and between needle holder 11 and collar 10".

In fact, the interference between tooth 23' of stem 14 and projection 33 of the extractor element must be such as to overcome the spring force to normally block the extractor element in advanced position, but at the same time it must allow the further advance of the stem relative to the extractor element when the latter is in stroke end position.

On the other hand, the force of spring 18 must be such as to overcome the interference between tooth 20 of collar 10" and annular recess 21 of needle holder 11.

It should be noted that the use of a conventional O-ring 24, in place of the special rubber caps to be fitted on the end of the syringe piston stem, besides considerably reducing the manufacturing cost of the syringe, favours the automated assembly of the syringe itself, since it allows using the high elasticity of the O-ring and its facility in being handled by automated assembly machines.

The syringe proposed herein is also especially safe in its regular use. This is especially due to the needle gluing to the needle holder, and to the connection thereof to the syringe cylinder collar. The needle gluing, which among the other things is also advantageously introduced into the needle holder from the outside, rather than being forced, that is, with interference, into the needle holder, allows preventing the risk of any scraping of the needle holder which could cause the suction of air which must then be ejected before the injection.

The glued needle further offers a considerably higher resistance to penetration and to the following extraction than that required by the standards of the field.

Also the connection of the needle holder to the cylinder collar described herein offers, as compared to the conventional connection by interference, a higher resistance to retraction, in any case higher than the values required by the standards.

It is clear that a person skilled in the art may make several changes and adjustments to the retractable needle syringe according to the present invention in order to meet specific and incidental needs, all falling within the scope of protection defined in the following claims.

The invention claimed is:

1. An improved retractable needle safety syringe comprising
    a hollow cylinder,
    a needle holder at an end of said hollow cylinder,
    a needle fixed to said needle holder,
    a piston with an operating stem sliding in said hollow cylinder, wherein said stem has an axial hole in which there is seated an extractor element having an end portion protruding from said axial hole and structure suitable for connecting to said needle holder, and wherein said extractor element is connected to a retraction pre/loaded spring, said extractor element and operating stem having connecting means suitable for determining an axial interference between stem and extractor element stronger than the force exerted by the spring on the extractor element and wherein, with the extractor element in stroke end position connected to the needle holder, the operating stem can be further pushed forward relative to the extractor element so that said connecting means release from each other, thus allowing the retraction of the extractor element with the connected needle holder into the axial hole of the operating stem wherein
    said connecting means comprises an internal annular tooth on the stem, an internal shoulder on the stem between the needle and the annular tooth, and an annular projection on the extractor element for interacting with said annular tooth and
    said annular tooth and said shoulder defining an annular internal recess on the stem, between the annular tooth and the shoulder, in which the annular projection of the extractor element is free to slide axially during forward movement of the piston and further comprising
    a sealing element mounted around said end portion of the extractor element protruding from said axial hole.

2. A syringe according to claim 1, wherein further advance of the operating stem compresses said sealing element against said end of the hollow cylinder.

3. A syringe according to claim 2, wherein said sealing element is an O-ring.

4. A syringe according to claim 3, wherein the bottom wall of said cylinder end has a substantially semi-cylindrical annular seat suitable for receiving said O-ring when compressed by the operating stem.

5. A syringe according to claim 3, wherein in said end portion of the extractor element there is provided an annular groove for seating said O-ring.

6. A syringe according to claim 2, wherein the hollow cylinder exhibits an increase of the internal diameter in the end portion thereof facing the needle holder so as to allow the sealing element to radially expand when pressed by the operating stem.

7. A syringe according to claim 1, wherein said extractor element has, in the portion thereof facing the needle holder, a seat or recess intended for connecting with an end portion of said needle holder.

8. A syringe according to claim 7, wherein said recess has an undercut and a seating aperture.

9. A syringe according to claim 8, wherein said end portion of the needle holder has a substantially truncated cone shape with a step or undercut, said end portion being intended for seating into said recess of the extractor element, said step being suitable for engaging in said undercut of said recess.

10. A syringe according to claim 1, wherein the needle holder is normally inserted in a collar that extends from said end of the hollow cylinder and is axially constrained to said collar thanks to the interaction between a tooth that extends from the inner surface of said collar and a corresponding recess provided in the needle holder.

11. A syringe according to claim 10, wherein said needle holder further comprises at least one slot such as to impart radial elasticity to said end portion of the needle holder.

12. A syringe according to claim 1, wherein the needle is secured to the needle holder by gluing.

13. A syringe according to claim 12, wherein the needle holder has a flared tip suitable for aiding the introduction of the needle from the outside and for being then filled with a suitable amount of glue.

* * * * *